United States Patent [19]

Hutchisson

[11] 4,079,007

[45] Mar. 14, 1978

[54] HEMODIALYSIS SYSTEM WITH MODULAR DIALYSATE MANIFOLD ASSEMBLY

[75] Inventor: James Thomas Hutchisson, Bellevue, Wash.

[73] Assignee: Union Carbide Corporation, New York, N.Y.

[21] Appl. No.: 720,673

[22] Filed: Sep. 7, 1976

[51] Int. Cl.² ............................................. B01D 13/00
[52] U.S. Cl. .................. 210/85; 210/321 R; 210/96 M
[58] Field of Search .................. 210/85, 87, 94, 96 M, 210/186, 321 B

[56] References Cited

U.S. PATENT DOCUMENTS

| 3,508,656 | 4/1970 | Serfass et al. | 210/90 |
|---|---|---|---|
| 3,515,275 | 6/1970 | Bowman | 210/22 R |
| 3,598,727 | 8/1971 | Willock | 210/2 |
| 3,703,959 | 11/1972 | Raymond | 210/87 |
| 3,754,649 | 8/1973 | Palubniak et al. | 210/103 |
| 3,809,241 | 5/1974 | Alvine | 210/87 |
| 3,814,249 | 6/1974 | Eaton | 210/87 |
| 3,878,095 | 4/1975 | Frasier et al. | 210/87 |
| 3,946,731 | 4/1976 | Lichtenstein | 128/214 R |

Primary Examiner—Frank A. Spear, Jr.
Assistant Examiner—E. Rollins Cross
Attorney, Agent, or Firm—Steven J. Hultquist

[57] ABSTRACT

A hemodialysis system comprising a modularized dialysate flow circuit manifold assembly. The manifold assembly is detachably secured in the hemodialysis system for ready replacement, whereby cross-contamination problems associated with multiple patient use of the system may be simply eliminated by the dedication of a manifold assembly to each patient.

7 Claims, 8 Drawing Figures

HEMODIALYSIS SYSTEM WITH MODULAR DIALYSATE MANIFOLD ASSEMBLY

BACKGROUND OF THE INVENTION

1. Field of the Invention

This invention relates generally to hemodialysis or artificial kidney systems for treatment of blood to remove waste impurities and undesirable components therefrom, and more specifically, to an improved hemodialysis system which overcomes cross-contamination problems associated with multiple patient use of the system.

2. Description of the Prior Art

Hemodialysis systems have been in general use for a number of years in the treatment of renal disease and disability, and have proven highly effective in providing artificial kidney functions for persons whose own natural kidneys are functionally impaired. In operation of the hemodialysis system, blood containing waste substances, such as for example urea, creatinine, excess electrolytic salts and water, is withdrawn from the body and flowed through a dialyzer in indirect mass transfer relationship with an aqueous dialysate solution. The dialyzer may be of various conventional types including a mass transfer member such as an extended surface elastomeric membrane or a hollow fiber bundle across which the waste substances are transferred by concentration gradient (solute impurities) or osmotic pressure (water) from the blood to the dialysate solution. From the dialyzer the blood which has thus been depleted in impurities is returned to the patient's body. The impurity-enriched dialysate solution from the dialyzer is either disposed of to waste or else is regenerated as by sorbent means to remove the waste impurities therefrom prior to being recirculated to the dialyzer for renewed mass transfer from the blood to the solution.

Although artificial kidney hemodialysis systems have demonstrated widespread acceptance and effectiveness in use, the majority of such systems which have been developed to date are costly, large in size and heavy in weight. Accordingly, these systems have heretofore been primarily employed in hospital renal treatment facilities and "satellite" dialysis centers. The geographically fixed locations of these hemodialysis facilities tends to significantly restrict the mobility of persons requiring dialysis treatment and involves inherent problems of accessibility and expense of travel for persons living in sparsely populated areas or otherwise at great distance from the treatment center. Due to the widespread character of renal disease and disability, the aforementioned problems affect substantial numbers of the population; at present, for example, maintenance hemodialysis is employed to preserve and protect the lives of approximately 24,000 persons in the United States alone. One of the greatest limitations of the dialytic regimen of treatment imposed on these patients is a forced alteration in life style as associated with the need for physical attachment to a hemodialysis system two or three times each week.

In an effort to ease the problems of geographical confinement of individual hemodialysis patients, patient travel in groups to areas served by dialysis centers within and outside of the United States has been organized by patient associations such as the National Association of Patients on Hemodialysis and Transplantation (NAPHT). Despite such efforts, however, medical and scheduling problems continue to impede free travel by the dialysis patient. For example, domestic dialysis centers may be filled to capacity and thus unable to accept guest patients. Foreign dialysis centers may be prohibitively expensive or absolutely closed to tourists or visiting patients.

Under the foregoing considerations, a particular problem is faced by patients who are hepatitus carriers, i.e., whose blood is Australian antigen positive, since they are generally excluded from all centers and thus are denied travel opportunities. Such exclusion results from the potential for cross-contamination of other patients from viral residues in the dialysate flow circuit of the hemodialysis system after use of the system by a hepatitus carrying patient. In conventional practice, the patient is joined to the dialyzer means in a closed flow loop by means of connecting lengths of flexible elastic tubing joined in turn to an arteriovenous shunt or fistula attached to the patient. Inasmuch as the dialyzer means, shunt and connective blood flow tubing are generally disposable or susceptible to sterilization for re-use without undue difficulty, the treatment of blood containing viral hepatitus by such equipment poses no particular difficulty. Nonetheless, during dialysis, such viral contaminants are able to diffusionally pass through the mass transfer surface, i.e., dialyzer membrane, from the infected blood to the dialysate solution flowed through the dialyzer.

The above described entry of contaminant species into the dialysate solution flow circuit during treatment results in a potential health hazard not associated with the blood flow circuit. This is because the dialysate solution flow circuit, unlike the blood flow circuit, is neither disposable in its entirety or readily adaptable to complete sterilization. Various physical characteristics of the dialysate solution in the dialysis system during treatment are extremely critical and, accordingly, a number of processing, monitoring, adjustment and control steps are typically employed in the dialysate solution flow circuit to insure effectiveness of the dialyzing operation and concomitant protection of the patient. For example, heating and temperature control means are generally utilized in the dialysate solution flow circuit to maintain the temperature of the dialysate solution therein at a proper level, e.g. 98°–100° F, to prevent undue heating or cooling of the blood by heat exchange with the dialysate solution and to prevent hemolysis. In addition, conductivity of the dialysate solution is characteristically monitored to insure that the solution has the proper level of salinity and electrolytic characteristics. Such provision is made so that vital components of the blood are not lost to the dialysate solution by ion diffusion across the mass transfer surfaces in the dialyzer. Finally blood leak detection means are generally coupled to the dialysate solution flow circuit to insure that only indirect mass transfer-i.e., diffusional and osmotic transfer of species across the dialyzer membrane- is occurring, without direct cross-leakage between the respective fluids in the dialyzer.

Due to the necessity of utilizing the above-mentioned monitoring and equipment means in the dialysate solution flow circuit, such flow circuits are not disposable in the manner of the previously-described blood flow circuits. Furthermore, such dialysate solution flow circuits are difficult to effectively sterilize due to the liklihood of damage to the sensitive monitoring and control components coupled into the circuit by chemical sterilizing agents or elevated temperature sterilizing techniques.

Thus, the problems associated with potential cross-contamination in dialysis treatment due to multiple patient use of the hemodialysis system are substantial and have not been satisfactorily overcome by the prior art.

Accordingly, it is an object of the present invention to provide an improved hemodialysis system for the treatment of blood to remove waste impurities therefrom.

It is also an object of the invention to provide a hemodialysis system in which cross-contamination problems associated with multiple patient use of the system are readily overcome.

It is another object of the present invention to provide a hemodialysis system of the above type which is compact, lightweight and readily portable.

Other objects and advantages of the invention will be apparent from the ensuing disclosure and appended claims.

SUMMARY OF THE INVENTION

This invention relates to a hemodialysis apparatus for treatment of blood to remove waste impurities therefrom. The apparatus includes dialyzer means through which waste impurity-containing blood and a dialysate solution are passed in indirect mass transfer dialyzing relationship for transfer of the waste impurities from the blood to the dialysate solution. Means are provided for supplying waste impurity-containing blood from a patient to the dialyzer means, and for returning waste impurity-depleted blood to the patient. Means are also provided for supplying dialysate solution to the dialyzer means along with means for discharging waste impurity-enriched dialysate solution from the dialyzer means forming a dialysate flow circuit.

In the improvement of the invention, the dialysate flow circuit includes a modularized dialysate solution manifold assembly. The assembly comprises a base support member, with dialysate solution flow passage means mounted on the base support member having an inlet and an outlet detachably coupled to the dialysate solution flow circuit for flow of dialysate through the flow passage means from the inlet to the outlet thereof. Means are included for heating the dialysate solution in the flow passage means to form warm dialysate solution. The apparatus includes means for sensing the temperature of the warm dialysate solution positioned downstream from the heating means and for adjusting the rate of heating of the dialysate solution by the heating means in response to the temperature sensing to maintain a predetermined dialysate solution temperature level. Monitor sensing means are positioned in the flow passage means including: means for detecting blood leakage into the dialysate solution, means for sensing the electrolytic conductivity of the dialysate solution, and means for sensing the dialysate solution temperature.

DESCRIPTION OF THE PREFERRED EMBODIMENTS

Figure 1:
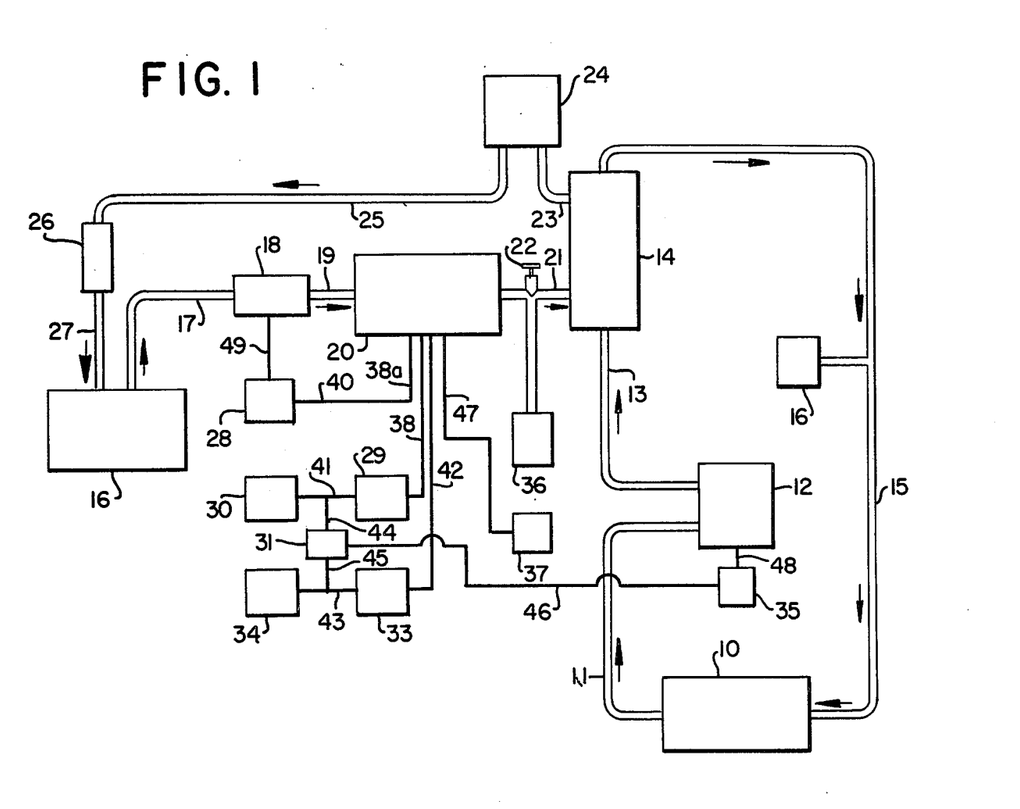
FIG. 1 is a generalized schematic block diagram of a hemodialysis system according to the present invention.

Referring now to the drawings, FIG. 1 shows a generalized schematic block diagram of a hemodialysis system such as is suitably employed in the practice of the present invention. In this illustrative system, the patient or hemodialysis subject 10 is joined in a closed loop blood flow circuit formed by blood flow tubing segments 11, 13 and 15 with dialyzer means 14, which may be of any suitable conventional type, as for example a parallel plate or hollow fiber bundle type. Waste impurity-containing blood is withdrawn from the patient as by means of an arterial fistula, cannula or shunt (not shown) and transferred by tubing segment 11 to peristaltic pump means 12, described more fully hereinafter, located upstream of the dialyzer means 14. By means of the pump means 12, the withdrawn waste impurity-containing blood is persitaltically pumped to advance blood through the above-described blood flow circuit. The speed of the peristaltic pump means is suitably controlled by motor speed control 35 coupled therewith, to obtain the necessary flow rate of blood through the blood flow circuit, as for example about 200 milliliters per minute.

After pumping by the peristaltic pump means 12, the waste impurity-containing blood is passed via line 13 through the dialyzer means 14 in indirect mass transfer dialyzing relationship with the dialyzing solution entering the dialyzer in line 21. As mentioned, the dialyzer means may suitably be of the parallel flow hollow fiber type comprising a bundled array of hollow fibers through which the waste impurity-containing blood is passed in countercurrent flow relationship with the dialysate solution flowing through the bundled array along the exterior surfaces of the hollow fibers. Waste impurity-depleted blood is returned from the dialyzer means to the patient by blood return line 15. The blood return line has pressure monitoring means 16, e.g. an anaeroid manometer, associated therewith to indicate the return blood pressure level, so as to permit the patient or other attendant to adjust the speed of the blood pump means or shut the apparatus down when the venous blood pressure level in the blood flow circuit increases or decreases to values outside of acceptable limits.

The waste impurity-enriched dialysate solution is discharged from the dialyzer means in line 23, passed to the peristaltic pump means 24 and peristaltically pumped therein to advance the dialysate solution through the dialysate solution flow circuit at sufficient rate for efficient transfer of waste impurities from the blood to the dialysate solution in the dialyzer means, as for example at a flow rate of about 500 milliliters/minute. The peristaltically pumped dialysate solution is discharged into line 25, in which it flows to adsorbent filter means 26. Adsorbent filter means 26 may in practice comprise a cannister of 200-300 grams of granular activated charcoal disposed in the dialysate solution flow circuit as shown downstream from the dialyzer means for removal of waste impurities from the waste impurity-enriched dialysate solution discharged from the dialyzer means. In this manner, by passage through the adsorbent filter means 26, the dialysate solution is partially sorptively regenerated before being passed in line 27 to dialysate solution supply container 16. The dialysate solution supply container 16 contains a suitable volume of solution for all or a portion of the dialyzing operation; for example, in accordance with the present invention, whereby the hemodialysis system may be provided in a small, compact, lightweight enclosure for ease of portability, as hereinafter described, the dialysate solution supply container may suitably be formed of a flexible, collapsible material such as polyethylene with a volume of between 10 and 30 liters.

From the supply container 16, the dialysate solution is withdrawn in line 17 and passed to heating means 18 wherein the dialysate solution is heated if necessary to approximately 98°-100° F. Such heating is carried out to yield a proper dialysate solution temperature to prevent undue heating or cooling of the blood by heat exchange with the dialysate solution and to prevent hemolysis. Warm dialysate solution is flowed from the heating means 18 in line 19 to the dialysate solution sensing assembly 20.

In the sensing assembly, means are provided for sensing the temperature of the dialysate solution together with means for converting the dialysate solution temperature sensing into a transmittable signal. This temperature sensing signal is transmitted by signal wires 38a and 40 to the temperature control circuit 28, which compares the temperature sensing signal with a set point value and generates a resultant control signal which is transmitted by control signal transmitting means 49 to the heating means 18 to provide the requisite level of heating for maintaining the set point value. In this manner, the rate of heating of the dialysate solution by the heating means is adjusted in response to the temperature sensing in the assembly 20 to maintain a predetermined dialysate solution temperature level.

Another temperature sensing signal from wire 38 is passed to amplifier 29 wherein the signal is amplified. The amplified temperature sensing signal is then passed in signal transmitting line 41 to the visual temperature display means coupled with the temperature sensing means by the aforementioned signal transmitting means for indication of the sensed dialysate solution temperature. Such visual display represents a safety means which permits the user or other attendant to take proper steps, i.e., shut down the dialysis system in the event of malfunction or failure of the temperature control circuit 28 or heating means 18.

Also in the sensing assembly 20, means are provided for sensing the electrolytic conductivity of the dialysate solution, together with means for converting the dialysate solutin electrolytic conductivity sensing into a transmittable signal. The conductivity sensing signal is transmitted by signal wire 42 to amplifier 33, and the resulting amplified conductivity sensing signal is transmitted by signal wire 43 to visual display means 34 for indication of the sensed dialysate solution electrolytic conductivity. Such monitoring of conductivity is desired to insure that the dialysate solution has the proper level of salinity and electrolytic characteristics, so that vital components of the blood are not lost to the dialysate solution by ion diffusion across the mass transfer surfaces in the dialyzer.

As shown, an audio alarm means 31 is coupled with the temperature sensing signal transmitting wire 41 and with the conductivity sensing signal transmitting wire 43 by the further respective signal transmitting wires 44 and 45. In this manner alarm means 31 is arranged for emitting an audible alarm when the sensed dialysate solution temperature or conductivity exceeds a predetermined value, thus notifying the user or attendant that one or both of these dialysate solution characteristics is outside of the desired limits by an extent which can then be readily determined by visual inspection of the display means 30 and 34 as an aid in determining the corrective action to be taken. As a further safety measure the audio alarm means may be coupled by signal wire 46 with motor speed control 35 which in turn is joined by signal wire 48 with the peristaltic blood pump 12 drive means, arranged so that the motor speed control means 35 is shut down by the transmitted audio alarm signal, thereby deactivating the peristaltic pump means in the blood flow circuit upon the emission of the audio alarm from the alarm means 31.

Finally, the dialysate solution sensing assembly 20 comprises means for detecting blood leakage into the dialysate solution flow stream together with means for converting the blood leakage detection into a transmittable signal. This signal is transmitted by signal wire 47 to blood leakage detection output means 37, which may suitably comprise visual display or audio alarm means. These blood leak detection means are provided to insure that only direct mass transfer -- i.e., diffusional and osmotic transfer of species across the dialyzer membrane -- is occurring, without direct cross-leakage between the respective fluids in the dialyzer.

From the dialysate solution sensing assembly 20, the dialysate solution is flowed through line 21, having negative pressure adjustment means 22 and negative pressure monitoring means 36 disposed therein, to the dialyzer means 14. Negative pressure is employed on the dialysate solution side of the membrane in the dialyzer means to effect water removal from the blood by ultrafiltration. The negative pressure on the dialysate side of the dialyzer means is adjusted by adjustment means 22 such as an eliptical flow valve and monitored by monitoring means 36 such as an anaeroid manometer.

In the FIG. 1 system, the dialysate solution supply and discharge means comprise a closed loop dialysate flow circuit made up of flow line segments 17, 19, 21, 23, 25 and 27 which join the dialyzer means 14 with the dialysate solution supply container 16, for batch recirculation of the dialysate solution through the dialyzer means. Alternatively, it is to be recognized that closed loop recirculation of dialysate could readily be eliminated in the illustrative system by deletion of the adsorbent filter means and dialysate solution return line 27. Such modification would provide a single pass, open loop dialysate solution flow circuit, wherein dialysate solution is withdrawn from the dialysate supply container 16, flowed through the dialysate solution heating means 18 and sensing assembly 20 to dialyzer 14, from which it is discharged to dialysate solution pump means 24 and finally passed out of the treatment system in line 25, to drain on other end use means.

Figure 2:
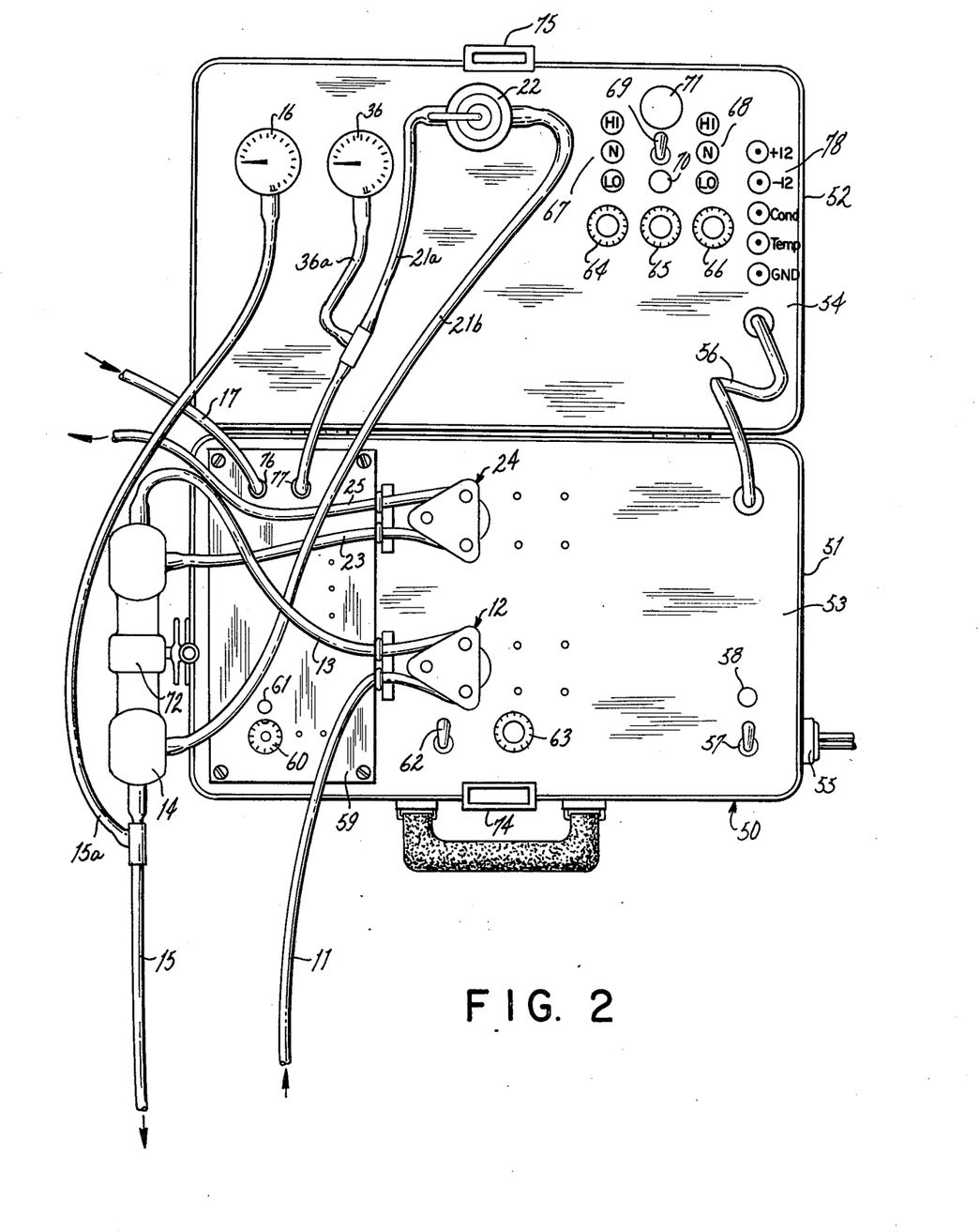
FIG. 2 is a plan view of a compact portable hemodialysis system according to the present invention, as contained in a unitary suitcase-type enclosure.

FIG. 2 is a plan view of a compact portable hemodialysis system according to the present invention, as contained in a unitary suitcase-type enclosure 50. The enclosure comprises lower section 51 with a lower facing panel 53 and upper section 52 with upper facing panel 54. As shown, the upper and lower sections are hingedly joined together and are fitted and retained together with the aid of complimentary locking numbers 74 and 75. When so fitted together, the enclosure is highly compact, measuring 21 inches in length by 12 inches in width by 6 inches in height. In practice, the enclosure casing may be formed of lightweight material such as aluminum so that the weight of the entire enclosure assembly is maintained sufficiently low for portability, as for example on the order of 24 pounds.

The system is designed to operate on conventional 120/220 volt alternating current, as provided to the system by the power line 55 entering the enclosure lower section 51 beneath facing panel 53. From the enclosure lower section, the power required for operation of the various monitoring and output display means on the right hand side of the upper section facing panel 54 as provided by panel connector line 56 linked with the power supply line 55 by a ± 12 volt direct current, 240 milliamp power supply beneath lower panel 53. Power is supplied to the system circuitry by means of the power switch 57 located below fuse holder 58 on the lower panel 53 and joined to the power supply line 55.

The blood flow circuit for the FIG. 2 system comprises tubing segments 11, 13 and 15 which may be of a conventional type formed of transparent polyvinylchloride or silicone elastomer. Waste impurity containing blood in accessed from the patient as for example by an arterio-venous fistula and is passed in the arterial feed line 11 to the peristaltic blood pump 12, as described more fully hereinafter, and the peristaltically pumped blood therefrom is passed through line 13 to the dialyzer 15. The dialyzer is of the parallel flow hollow fiber type previously described having about 1.50 meters$^2$ of membrane mass transfer exchange area for dialysis. In the dialyzer, the waste impurity constituents of the blood such as urea, uric acid and creatinine diffuses from the blood across the membrane into the dialysis solution. Water removal from the blood is carried out by ultrafiltration effected by using up to 350 mm Hg negative pressure on the dialysate solution side of the membrane and up to 500 mm Hg overall trans-membrane negative pressure. Typically 1 to 2 liters of water is removed during the dialysis treatment.

From the dialyzer 14, which is supportively positioned adjacent the enclosure unit by means of a clamp and stand assembly joined to the exterior side wall of the enclosure lower section, the waste impurity-depleted blood is returned in line 15 to the patient. Line 15a is joined to blood return line 15 and communicates with venous pressure manometer 16 which monitors the return blood pressure over the pressure range of from 0 to 350 mm Hg.

The dialysate solution flow circuit for the FIG. 2 system comprises tubing segments 17, 21a, 21b, 23 and 25, which also may be of a conventional type formed of polyvinylchloride or silicone rubber. From the dialysate solution supply means, which may for example comprise a 21 liter collapsible polyethylene container holding dialysate solution which is changed twice to fresh solution during the course of a 4 to 5 hour dialysis treatment, the dialysate solution is passed in line 17 into the dialysate manifold assembly as hereinafter described in greater detail, through the inlet opening 76 in base support plate member 59. The base support plate member 59 is detachably secured to the lower panel 53 in enclosure 50 by suitable screw or bolt fastener means. In the dialysate manifold assembly the dialysate solution is heated to the extent necessary to maintain temperature of the solution at about 98° F and temperature, conductivity and blood leak are monitored. The dialysate solution heating means associated with the dialysate manifold assembly are activated by power switch 62. An adjustment dial 60 is provided on the top side of base support plate member 59 for manual adjustment of the set point control temperature for the dialysate heating means, and indication lamp 61 above adjustment dial 60 indicates when the heating means have been activated by the dialysate solution temperature control circuit.

From the dialysate solution manifold assembly, warm dialysate solution passes through the outlet opening 77 in base support plate member 59 into line 21a. Line 21a is coupled via line 36a with the negative pressure manometer 36, for visual monitoring of the dialysate solution negative pressure in the range of 0 to 350 mm Hg. From line 21a the dialysate solution flows through elliptical control valve 22, which is manually adjustable for varying the negative pressure of the dialysate solution, depending on the water content of the waste impurity-containing blood being dialyzed and the desired degree of removal of water therefrom. The elliptical valve 22 is connected on its downstream side with line 21b through which the dialysate solution flows to the dialyzer 14 for mass transfer of waste impurities from the blood to the dialysate solution. Waste impurity-enriched dialysate solution is discharged from the dialyzer 14 in line 23 and passed to the peristaltic dialysate solution pump 24. The dialysate solution is advanced by the peristaltic pump 24 through line 25 for recirculation to the aforementioned dialysate supply container.

The power for all sensors in the dialysate manifold assembly, as well as the temperature control circuit is provided by the same DC power supply means positioned beneath lower section panel 53 as supplies power to the electronics monitoring module on the upper right hand corner of upper section panel 54 through connecting line 56. All sensors in the dialysate solution manifold assembly are monitored and read out on the upper section panel monitoring module. Panel calibration controls 64, 65 and 66 are respectively provided for the conductivity, temperature and blood leak detection parameters monitored in the dialysate solution manifold assembly, together with upper section panel test points 78 to facilitate calibration. Alarm limites are fixed for temperature and conductivity, and are adjustable for blood leak detection, by varying the blood leak detection calibration setting of adjustment dial means 65. A blood leak detection warning light 70 is provided which is responsively coupled with blood leak sensing means in the dialysate solution manifold assembly, together with an audio bood leak detection alarm 71 likewise coupled to the blood leak sensing means. The visual displays 67 and 68 for dialysate solution temperature and conductivity conditions, respectively, are provided by red light emitting diodes (LEDs) indicating high (HI) or low (LO) conditions, i.e., values outside of the predetermined range limits. A green LED (N) indicates normal operating conditions. The audio alarm 71, also coupled to the dialysate solution manifold assembly temperature and conductivity sensing means as described in connection with FIG. 1 hereinabove, provides a 2.2 KH$_z$ 80 decibel signal. For convenience, a switch 69 permits disconnection of the audio alarm 71 while retaining the respective visual alarms. The dialysate solution electrolytic conductivity alarm limits are at ± 1% of the calibration point, corresponding to 13.5 millimhos nominally. Dialysate solution temperature alarm limits are at ± 2° of the calibration point, corresponding to 98° F nominally.

The peristaltic blood pump 12 and peristaltic dialysate solution pump 24 in the FIG. 2 system are identically dimensionally sized. The pump heads of these pumps are separately driven by double gear reduction shunt wound D.C. motor drive means. Blood flow rate from the pump is controlled by variable motor speed control means 63, by which the drive means are coupled with the blood pump head assembly for rotation thereof at a speed in the range of from 50 to 400 rpm, to induce pulsatile flow in the blood being advanced by the pump through the blood flow circuit. Preferably, the blood flow rate is maintained at a value of about 200 milliliters/minute during dialysis. The dialysate solution peristaltic pump 24 is identical in design to the peristaltic blood pump 12, but has associated drive means coupled to its pump head assembly for rotation thereof at a speed in the range of from 200 to 600 rpm, to provide a dialysate solution flow rate of about 500 milliliters/minute and induce pulsatile flow in the dialysate solution being advanced through the dialysate solution flow circuit and passed through the dialyzer means.

Figures 3, 7:
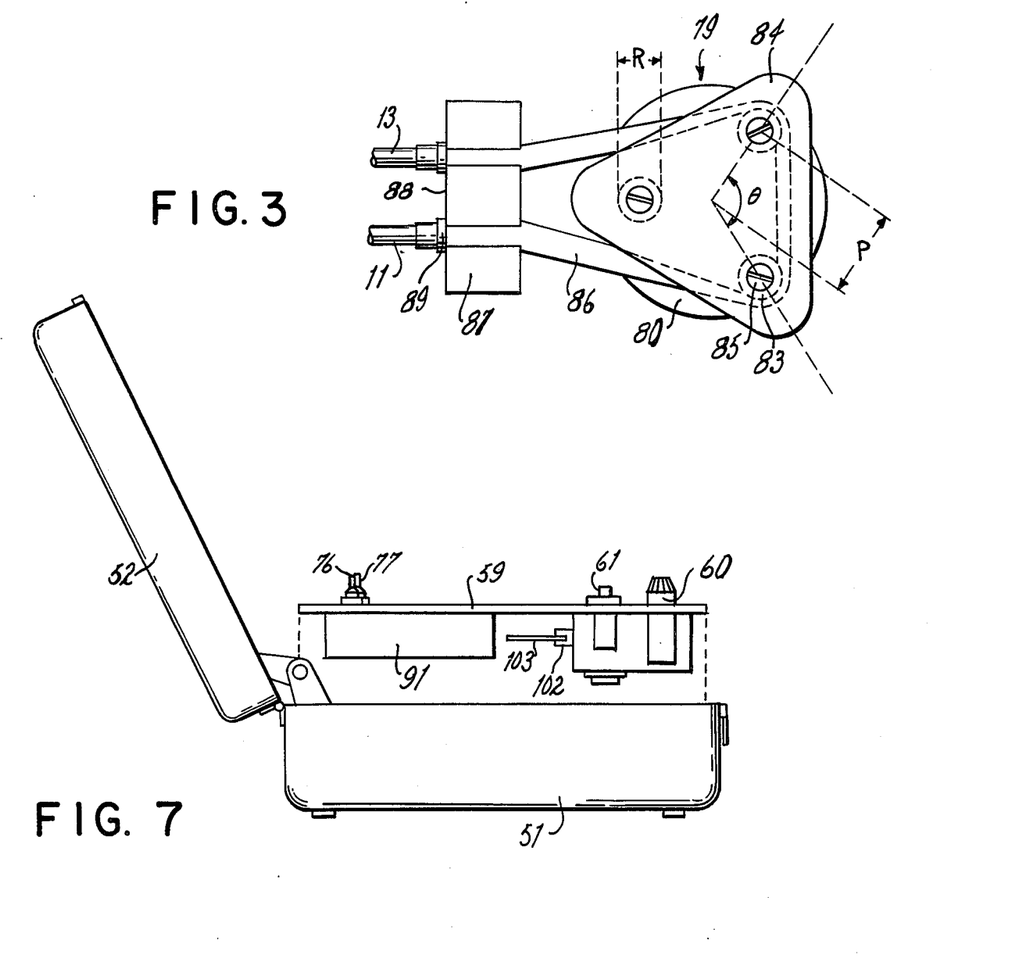
FIG. 3 is a perspective view of the peristaltic blood pump employed in the FIG. 2 hemodialysis system.
FIG. 7 is a side elevational view of a hemodialysis system of a type as shown in FIG. 2, showing the details of construction of the dialysate manifold assembly.

FIG. 3 is a perspective view of the peristaltic blood pump 12 employed in the FIG. 2 hemodialysis system. As shown the pump head assembly 79 includes the pump head base member 80 inset with set screws 81 for rigidly attaching the pump head assembly to a rotatable shaft coupled with the motor drive means therefor. In this fashion the pump head base member is positioned for rotation about a fixed axis. Mounted on the pump head base member by bolt or screw fastener means for independent rotation about respective axes parallel to the base member fixed axis are three circumferentially spaced apart rollers 83 disposed between the lower and upper tubing guide members 82 and 84, respectively.

Figure 4:
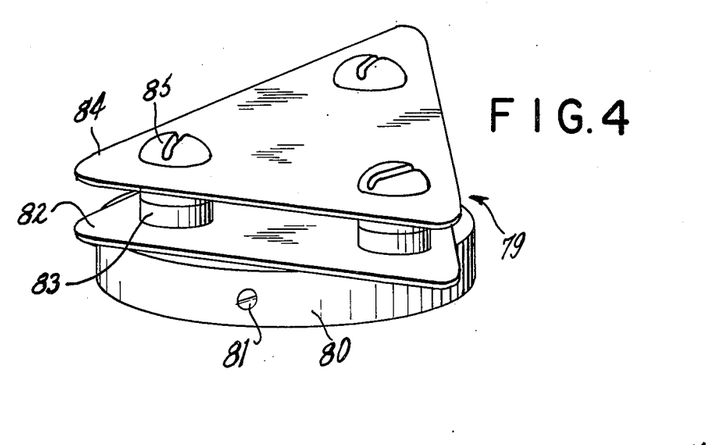
FIG. 4 is a plan view of the peristaltic blood pump, flexible resiliant tubing pumping section and anchor block assembly employed in the FIG. 2 hemodialysis system, showing the dimensional characteristics thereof.

FIG. 4 is a plan view of the peristaltic blood pump, flexible resiliant tubing pumping section and anchor block assembly employed in the FIG. 2 hemodialysis system, showing the dimensional characteristics thereof. As shown, the blood flow circuit comprises tubular segments 11 and 13 joined to a flexible resiliant tubing pumping section 86 through which blood is pumped. An anchor block 87 is provided for anchoring the end segments of the flexible resiliant tubing pumping section 86 such that the tubing forming the pumping section is tensionally extended around the pump head assembly 79. In this arrangement the tubing is simultaneously engaged and compressed by at least two of the circumferentially spaced apart rollers 83 with at least partial closure of the tubing at the points of compression, as shown. The rollers 83 are mounted for longitudinal movement of the points of compression along the tubing during rotation of the pump head assembly to advance blood through the tubing. As illustrated the pumping section of flexible resiliant tubing is anchored at the face 88 of the anchor block 87, opposite the side on which the pump head assembly is positioned, by means of the flanged connector means 89 attached to the end segments of the flexible resiliant tubing pumping section and to the ends of the blood flow lines 11 and 13.

In the preferred practice of the present invention, high frequency pulsatile flows of blood are passed through the dialyzer means of the hemodialysis system to reduce blood film mass transfer resistances in the dialyzer means. For such purpose, the peristaltic blood pump means comprises three rollers mounted on the base member, each roller having a diameter R, as shown in FIG. 4, of between 0.25 and 0.75 inch and circumferentially spaced apart at an angle of 120° from the other rollers with a radial distance P between the roller axis and pump head assembly member 80 fixed axis of from 0.50 to 1.25 inches. The preferred practice also employs a flexible resiliant tubing pumping section length, as measured longitudinally along the tubing between the anchored end segments thereof, of from 6.0 to 6.75 inches, a wall thickness of from 0.03 to 0.10 inch and an internal diameter of from 0.18 to 0.25 inch, with drive means coupled to the pump head assembly for rotation thereof at a speed in the range of from 50 to 400 rpm.

Although peristaltic pump means have been employed by the prior art for pumping blood in hemodialysis system blood flow circuits, the prior art has not been able to achieve the intensity of pulsatile flow which is realized in the above arrangement. This is a consequence of the striking difference in physical dimensions and operating rotational speeds between the peristaltic blood pump means of the above arrangement and the pump means of the prior art. As compared with conventional blood pumps of the type generally used in hemodialysis systems, the peristaltic blood pump means of the above arrangement are only about one-tenth of the size of conventional pumps and operate at about 10 times the rotational speed of conventional pumps. The reason that the prior art has not attempted to use pumps having such small size and high rotational speeds is due to the expected occurrence of excessive levels of hemolysis under such dimensional characteristics and operating conditions. For this reason and in an effort to minimize hemolysis effects, the prior art has utilized massive peristaltic pump means and slow rotational pump speeds to pump blood through the hemodialysis system. This in turn has severely impeded the development of small, light and inexpensive portable hemodialysis sytems such a suitably employed in the instant invention.

Unexpectedly, the peristaltic blood pump means described above have been found to be remarkably free from hemolysis and related cell damage effects in use. The reason for such beneficial and wholly unexpected behavior is not fully understood, It may be that the intensely pulsatile character of the blood flow associated with the high rotational pump speeds together with the short pumping volume segment length (length along the tubing section between the points of compression of successive rollers against the tubing section) in some manner act anomalously to "cushion" the blood being pumped so as to minimize adverse pumping compression effects. Nonetheless, we do not wish to be bound by any particular theory by way of explanation of the remarkably low incidence of such adverse pumping compression effects, subject only to specific essential system features and elements herein described.

Under the above arrangement, the peristaltic pumping section of tubing must be both flexible and resiliant so that the tubing, even though under continuously varying tensional and compressive load conditions, does not tend to fatigue and crack in use and so that the tubing quickly reacquires its undeformed shape and dimensions after the direct bearing of roller compression on the tubing is released as the roller moves along the length of the tubing. Tubing pumping sections formed of silicone elastomers have been found to satisfy the foregoing requirements and to be particularly useful in the practice of this invention. As mentioned, the rollers mounted on the pump head assembly must have a diameter of between 0.25 and 0.75 inch. At diameter values below 0.25 inch, the roller tends to be too small, imparting insufficient thrust to the blood as the roller engages the tubing pumping section, with resulting loss of efficiency in the pumping operation. If the roller diameter exceeds about 0.75 inch an excessive amount of tubing is occluded when the roller engages the tubing pumping section, thereby undesirably lowering the instantaneous volumetric pumping capability of the pump means and hence the pumping efficiency of the pump means. The peristaltic pumps employ three rollers circumferentially spaced apart at an angle of 120° from the other rollers. If less than three rollers were employed, the pulsatile wave frequency produced by the pump means would be reduced by at least half since the wave or pulsation frequency is proportional to the number of rollers in the pump head assembly. As a result, the pump means would have to operate at correspondingly, unacceptably circumferentially high rotational speed to achieve the same pulsatile flow characteristics as are desirably realized with three pump head assembly rollers. If more than three pump head assembly rollers are employed, fabrication of the pump head assembly becomes increasingly complex due to the use of additiional component parts and the requirement of close dimensional tolerances therefor; in addition, with more than three rollers, the frequency of the pulsatile flow output of the pump is incrased to such a level that undesirable aberrant flow effects, as for example pulsatile wave interference and short-circuiting, become significant. The three rollers employed in the pump head assembly are most efficiently uniformly circumferentially spaced apart — i.e., circumferentially spaced apart by an angle of 120° — in order to provide an effective regular and uniform output pulsatile flow of blood from the pump means.

The peristaltic pump also desirably employs a radial distance, as measured between a given roller axis and the pump head assembly base member fixed axis, of from 0.50 to 1.25 inches. The reasons for such limits are complimentary to the reasons discussed above for the roller diameter limits. If the radial distance is less than about 0.50, an excessive amount of tubing is occluded when the roller engages the tubing pumping section, thereby undesirably lowering the instantaneous volumetric pumping capability of the pump means and hence the pumping efficiency of the pump means. On the other hand, if the radial distance is greater than about 1.25 inches, the unsupported lengths of tubing between adjacent rollers tend to be too long relative to the size of the rollers contacting the tubing, so that the roller tends to impart insufficient thrust to the blood as the roller engages the tubing pumping section, with resulting loss of efficiency in the pumping operation. The flexible resiliant tubing pumping section under the present invention must have a length as measured longitudinally along the tubing between the anchored end segments thereof, of from 6.0 to 6.75 inches, a wall thickness of from 0.03 to 1.10 inch, and an internal diameter of from 0.18 to 0.25 inch. As the pumping section tubing length, e.g., measured longitudinally along the tube between the coupling members 89 in the illustrative FIG. 4 embodiment, decreases below about 6.0 inches, a point is reached where it is not physically possible to extend the tubing around the pump head assembly with adequately low tension. At length values above about 6.75 inches, the length of the tubing tends to overmatch the dimensions of the pump head assembly, with the result that if the tubing is anchored with the proper tension for at least partial closure at the points of compression of the rollers against the tubing, such tensioning also tends to at least partially close significant lengths of the tubing between thre adjacent rollers. A tubing wall thickness of at least 0.03 inch is necessary to insure the leak-tight integrity of the pumping section, which is subjected to clontinuous and rapid swings of tensional extension and relaxation such as tend to unduly fatigue and rupture tubings of lesser thickness. At tubing thicknesses above 0.40 inch, the pumping section tends to become too rigid for adequate and proper compression by the rollers. If the internal diameter of the tubing pumping section decreases below about 0.18 inch, there tends to be an improper match between the tube size and the roller size requirements, with the result that an excessive volume of tubing is occluded with corresponding reduction in blood pumping efficiency for the system. On the other hand, at tubing internal diameter values above 0.25 inch, an excessive amount of tension is required for at least partial closure of the tubing at the points of compression by the rollers, beyond the tensile strength properties of most otherwise suitable flexible resiliant tubing materials of construction.

Finally, the peristaltic blood pump means desirably employ drive means coupled to the pump head assembly of the blood pump for rotaton thereof at a speed in the range of from 50 to 400 rpm, to induce pulsatile flow in the blood being advanced through the flexible resiliant tubing pumping section. As the rotational speed of the pump head assembly decreases to values below about 50 rpm, the flow regime changes from turbulent to laminar, with a disproportionate reduction in mass transfer efficiency for the dialysis system; at such low rpm values, the intensity of the pulsatile flow from the peristaltic pump is relatively low and does not compensate for the transition from the turbulent to the laminar flow regime. At rotational speeds above 400 rpm, the intensity of the peristaltic pumps pulsatile flow output is increased to such extent that hemolysis effects finally become significantly large. Preferably, the drive means are coupled to the pump head assembly of the peristaltic blood pump for rotation thereof at a speed in the range of from 180 to 240 rpm.

In a preferred method aspect under the foregoing, the previously described peristaltic blood pump and broad operational pump head assembly rotational speed range of 50 to 400 rpm correspond to the production of a pulsatile flow in the waste impurity-containing blood withdrawn from a patient by the peristaltic pumping having a frequency of between 100 to 800 cycles/minute whereby the pulsatile flow of blood is passed through the dialyzer means to reduce blood film mass transfer resistance therein, in accordance with the formula $$f = S \times (N - 1)$$

wherein $f$ = peristaltic pumping pulsatile flow frequency, cycles/minute, $S$ = pump head assembly rotational speed, rpm, and $N$ = number of pump head assembly rollers (= 3).

Accordingly, in preferred practice, the pulsatile blood flow has a frequency of between 200 and 400 cycles/minute.

In accordance with the present invention, the dialysate solution flow circuit joined to the dialyzer means may suitably include a flexible resiliant tubing pumping section through which dialysate solution is pumped, with further peristaltic pump means coupled to the flexible resiliant tubing section in the dialysate solution flow circuit in the same manner as the peristaltic pump in the blood flow circuit, as for example is shown in the FIG. 2 embodiment of the invention. In one arrangement under this embodiment, the further peristaltic pump means and the flexible resiliant tubing section in the dialysate solution flow circuit are dimensionally sized identically with the peristaltic pump means and the flexible resiliant tubing section in the blood flow circuit. Drive means are coupled to the pump head assembly of the further peristaltic pump means for rotaton thereof at a speed in the range of from 200 to 600 rpm, to induce pulsatile flow in the dialysate solution being advanced through the flexible resiliant tubing pumping section of the dialysate solution flow circuit and passed through the dialyzer means. The reason for such higher range of rotational speed values for the peristaltic dialysate solution pump relative to the speed range for the peristaltic blood pump is that in the dialysate solution flow circuit a substantially higher fluid flow rate, e.g. about 450-500 milliliters dialysate solution/minute, is required, as opposed to a flow rate of approximately 200 milliliters blood/minute for the blood flow circuit. Accordingly, if the further peristaltic pump means and the flexible resiliant tubing section in the dialysate solution flow circuit are dimensionally sized identically with the peristaltic pump means and the flexible resiliant tubing section in the blood flow circuit, the rotational speed of the dialysate solution pump head assembly will be determined solely by the volumetric flow rate requirements of the dialysate solution flow circuit, and will not depend on laminar to turbulent flow transition conditions or fluid damage considerations as in the case of the blood flow circuit. Nonetheless, the above-mentioned dialysate solution pump head assembly rotational speed range of 200 to 600 rpm provides an intense pulsatile flow in the dialysate flow circuit which reduces th dialysate film mass transfer resistance in the dialyzer and thus additionally enhances the dialyzing efficiency of the hemodialysis system. In accordance with the previously stated formula, the method aspect associated with the above-described dialysate solution flow circuit relates to peristaltically pumping dialysate solution in the dialysate flow circuit to produce a pulsatile flow of the dialysate solution therein having a frequency of between 400 to 1200 cycles/minute. In preferred practice, drive means are coupled to the pump head assembly of the dialysate solution peristaltic pump means for rotaton thereof at a speed of from 450 to 500 rpm. Of course, it will be appreciated that it may be desirable or necessary to deploy pump means other than peristaltic pump means in the dialysate solution flow circuit to circulate fluid therein, as for example, eccentric ring type pumps or gear pumps. Nonetheless, the use of peristaltic pump means, of the type described above in connection with the blood flow circuit, in the dialysate solution flow circuit permits a significant reduction in dialysate fluid film mass transfer resistance in the dialyzer to be realized, with concomitant increase in overall system dialyzing efficiency.

Figure 5:
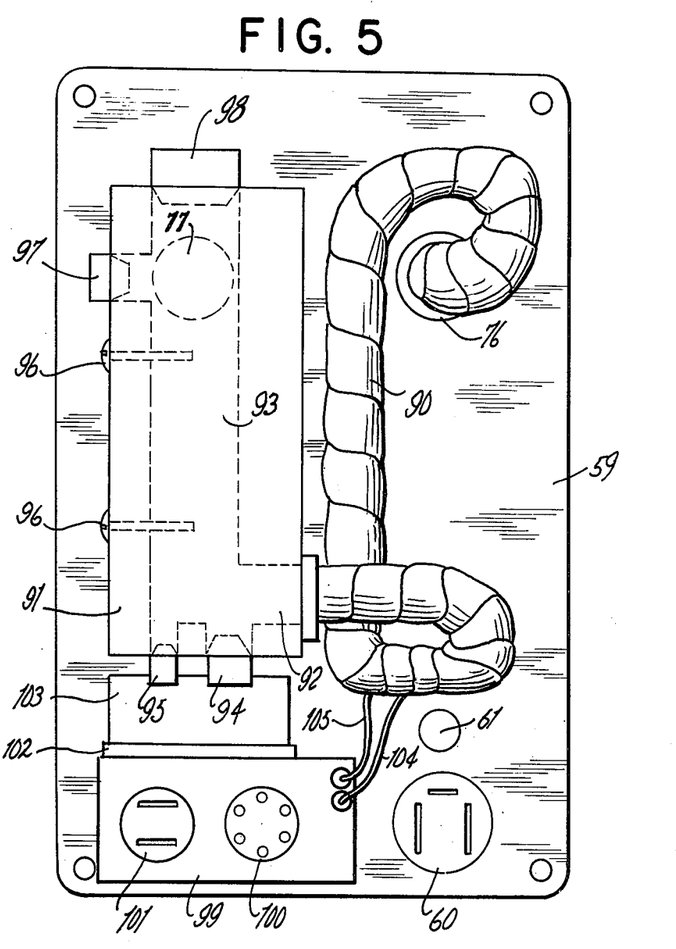
FIG. 5 is a bottom view of the modularized dialysate flow circuit manifold assembly for the FIG. 2 hemodialysis system, showing the details of construction thereof.

FIG. 5 is a bottom view of the modularized dialysate flow circuit manifold assembly for the FIG. 2 hemodialysis system, showing the details of construction thereof. From the dialysate solution supply container, as shown in FIG. 1, the dialysate solution flows through a connecting tubing segment and passes into the inlet opening 76 in base support member 59 of the manifold assembly to the heater 90. Heater 90 comprises a thermally conductive tubular passage through which the dialysate solution flows for heating therein by insulated resistance heating strip means spirally wound around the tubular passage. The wound heating strip is energized by current carrying electrical wires 104 and 105 joined thereto from the electronics enclosure 99. In the heater 90, the dialysate solution is warmed if necessary to a temperature in the vicinity of 98° F and then flowed into the manifold sensor block 91, which is a flow enclosure means containing an extended dialysate solution flow passage 93, along which are positioned temperature control sensing means 94 and photocell blood leak detection means adjacent the flow passage inlet 92.

Along the main length of the dialysate solution flow passage 93 are positioned a pair of spaced apart electrodes 96 as dialysate solution electrolytic conductivity sensing means. At the outlet end of the manifold sensor block 91, adjacent to the outlet opening 77 in the base support member 59, are disposed a thermistor temperature monitoring sensor 97 and a photocell blood leak detector light source 98. The dialysate solution discharged from the manifold sensor block 91 through outlet opening 77 flows into a connecting tubing segment attached on the top side of the base support member 59 to negative pressure monitoring and adjustment means before passage to the dialyzer means.

In the illustrative manifold assembly, the temperature control sensing means 94 may suitably be joined with a conventional integrated circuit temperature transducer 103 mounted in socket 102 on the electronics enclosure 99. Transducer circuit 103 is optically coupled with a silicon rectifier gate means in the electronics enclosure 99 which controls the current signal transmitted in wires 104 and 105 to the heating strip for heat exhcanger 90. In this manner, the thermo-control circuit is arranged to maintain the temperature of th dialysate solution to within ±0.5° F about an adjustable control set point. All sensing means in the manifold sensor block 91—blood leak sensor 95, electrolytic conductivity sensors 96, and temperature sensor 97—are monitored and read out on the electronics display section of the upper section panel 54, as shown and described in connection with the FIG. 2 embodiment of the invention.

In the illustrated manifold assembly, the sensor block 91 may suitably be formed of nylon, as a unitary block structure which is easily removed for cleaning and repair. The manifold assembly further includes heater indicator lamp 61 suitably coupled to the silicon rectifier gate means in the electronics enclosure 99, to visually indicate when the heating means have been activated, and temperature calibration potentiometer 60 for adjustment of the set point dialysate solution temperature. The electronics enclosure 99 provides power and signal readout connection means including low voltage sensor signal connector 100 which is joined to the aforementioned upper section panel display module and 120 volt AC connector 101 to supply power to the heating means associated with the manifold assembly.

Figure 6:
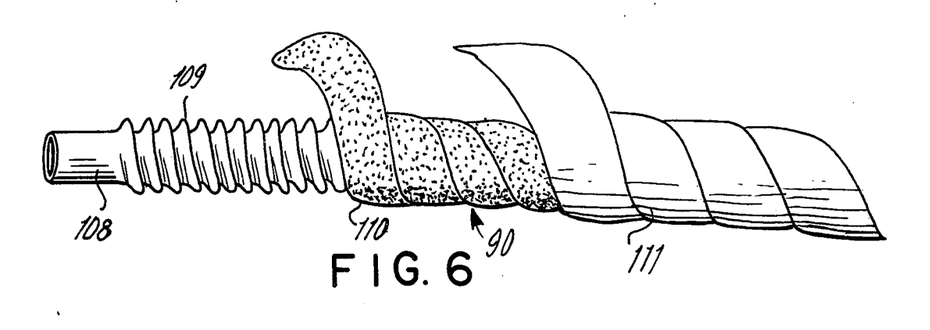
FIG. 6 is a partially assembled view of a section of the tubular heating means employed in the FIG. 5 manifold assembly, showing the construction thereof.

FIG. 6 is a partially assembled view of a section of the tubular heating means employed in the FIG. 5 manifold assembly, showing the construction thereof. As illustrated, the dialysate solution heating means 90 comprises a tube 108 the wall of which is helically ribbed with corrugated ribs 109. The tube 108 may be formed of 316 Stainless Steel, with a nominal outer diameter of ½ inch and a length of 24 inches. The helical ribbing of the tubing walls creates a vortex flow of dialysate solution through the tubing which in turn facilitates efficient heat transfer to the dialysate solution from the heating tape 110 spirally wound around the tubing 108. The tape 110 suitably comprises an insulated 288 watt heating tape. Aluminum foil 111 is spirally wrapped around the heating tape 110 to improve the heat transfer efficiency of the tape by reducing radiative heat losses therefrom and to mechanically protect the heating tape.

FIG. 7 is a side elevational view of a hemodialysis system as shown in FIG. 2, showing the details of construction of the dialysate manifold assembly,. As shown, the base support member 59 is provided in the form of a plate or planar sheet. In this form, the manifold assembly may be detachably secured in the hemodialysis system for ready replacement, with the inlet and the outlet of the dialysate solution flow passage means of the manifold assembly detachably coupled to the dialysate solution flow circuit as by coupling means 76 and 77 whereby cross-contamination problems associated with multiple patient use of the system may be simply eliminated by the dedication of a manifold assembly to each patient.

Figure 8:
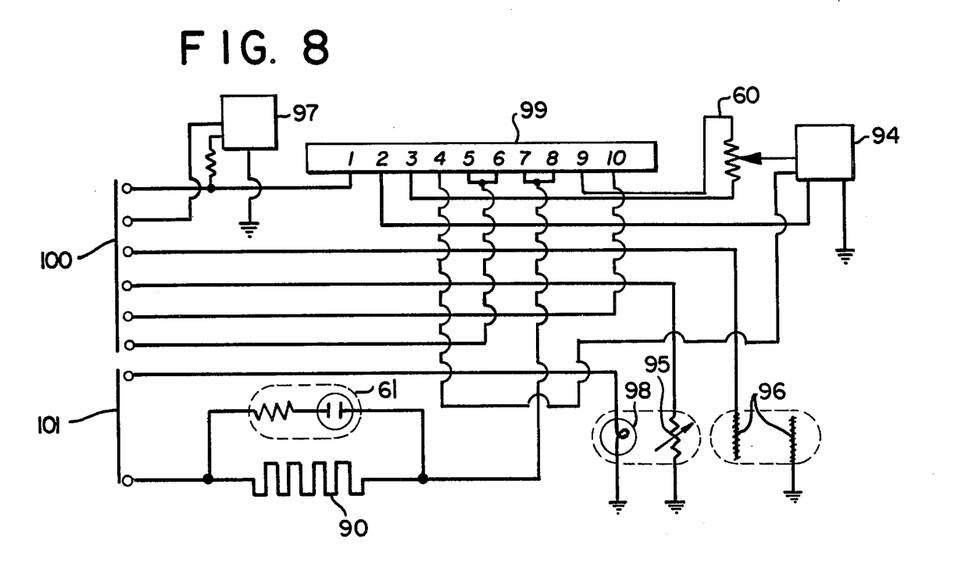
FIG. 8 is a schematic wiring diagram for the dialysate manifold assembly of FIGS. 5 and 7.

FIG. 8 is a schematic wiring diagram for the dialysate manifold assembly of FIGS. 5 and 7. The connections of the electrolytic conductivity sensing electrodes 96, blood leak sensing means 95, blood leak light source 98, strip heater 90, pilot lamp 61, dialysate solution temperature control sensor 94, temperature control adjustment potentiometer means 60 and the dialysate solution temperature sensing means 97 with the electronics enclosure circuit connector 99, low voltage signal connector 100 and 120 volt A.C. connector 101 are clearly shown.

Although preferred embodiments of the invention have been described in detail it will be appreciated that other embodiments are contemplated only with modifications of the disclosed features, as being within the scope of the invention.

What is claimed is:

1. In a hemodialysis apparatus for treatment of blood to remove waste impurities therefrom, including: dialyzer means through which waste-impurity containing blood and a dialysate solution are passed in indirect mass transfer dialyzing relationship for transfer of said waste impurities from said blood to said dialysate solution; means for supplying waste impurity-containing blood from a patient to said dialyzer means; means for returning waste impurity-depleted blood to said patient; and means for supplying dialysate solution to said dialyzer means and means for discharging waste impurity-enriched dialysate solution from said dialyzer means forming a dialysate flow circuit, the improvement wherein said dialysate flow circuit includes a modularized dialysate solution manifold assembly and tubing segments for flowing dialysate solution to and discharging dialysate solution from said manifold assembly, said manifold assembly comprising:
    (a) a base support plate member with main flat top and bottom surfaces having spaced-apart dialysate solution inlet and outlet openings therein, with coupling means associated with said inlet and outlet openings on the main top surface of said base support plate member for detachably joining the manifold assembly with said dialysate solution tubing segments;
    (b) means positioned on the main bottom surface of said base support plate member comprising a tubular passage having an inlet end communicating with said dialysate solution inlet opening for flow of dialysate solution therethrough to an outlet end of said tubular passage and means for heating said dialysate solution in said tubular passage to form warm dialysate solution;
    (c) means for sensing the temperature of said warm dialysate solution positioned downstream from said heating means and for adjusting the rate of heating of said dialysate solution by said heating means in response to said temperature sensing to maintain a predetermined dialysate solution temperature level;
    (d) a flow enclosure means positioned on the main bottom surface of said base support plate member containing a dialysate solution flow passage having an inlet joined to the outlet end of said tubular passage of (b) and having an outlet communicating with said dialysate solution outlet opening for flow of dialysate solution therethrough, with monitor sensing means positioned in said dialysate solution flow passage including: means for detecting blood leakage into said dialysate solution, means for sensing the electrolytic conductivity of said dialysate solution, and means for sensing said dialysate solution temperature,
the apparatus being constructed such that said manifold assembly may readily be detached from said dialysate solution tubing segments and separably removed from the remainder of said hemodialysis apparatus.

2. Apparatus according to claim 1 wherein said dialysate solution temperature sensing means of (c) is positioned in said dialysate solution flow passage of (d).

3. Apparatus according to claim 1 wherein said means for heating said dialysate solution comprise an insulated resistance heating strip means wound around said tubular passage.

4. Apparatus according to claim 1 further comprising: means for converting said temperature sensing of means (d) into a transmittable signal; means for transmitting said temperature sensing signal; visual display means coupled with said temperature sensing means by said signal transmitting means for indication of said sensed dialysate solution temperature; means for converting sensed dialysate solution electrolytic conductivity into a transmittal signal; means for transmitting said electrolytic conductivity sensing signal; and visual display means coupled with said electrolytic conductivity sensing means by said conductivity signal transmitting means for indication of said sensed dialysate solution electrolytic conductivity.

5. Apparatus according to claim 3 further comprising: audio alarm means coupled with said temperature sensing signal transmitting means and with said conductivity sensing signal transmitting an audible alarm when the sensed dialysate solution temperature or conductivity exceeds a predetermined value.

6. Apparatus according to claim 1 wherein said means for supplying waste impurity-containing blood from a patient to said dialyzer means include a flexible resilient tubing pumping section through which blood is pumped, with said blood supplying means and said means for returning waste impurity-depleted blood to said patient forming a blood flow circuit, further comprising: peristaltic pump means with a rotatable pump head assembly including a base member positioned for rotation about a fixed axis with a plurality of circumferentially spaced apart rollers mounted thereon for independent rotation about respective axes parallel to the base member fixed axis; means for anchoring the end segments of the flexible resilient tubing pumping section such that the tubing is tensionally extended around the pump head assembly, being simultaneously engaged and compressed by at least two of said circumferentially spaced apart rollers with at least partial closure of the tubing at the points of compression, said rollers being mounted for longitudinal movement of the points of compression along the tubing during rotation of said pump head assembly to advance blood through said tubing.

7. In a hemodialysis apparatus for treatment of blood to remove waste impurities therefrom, including: dialyzer means through which waste-impurity containing blood and a dialysate solution are passed in indirect mass transfer dialyzing relationship for transfer of said waste impurities from said blood to said dialysate solution; means for transferring waste impurity-containing blood from a patient to said dialyzer means including a flexible resilient tubing pumping section through which blood is pumped and means for returning waste impurity-depleted blood to said patient forming a blood flow circuit; means for transferring dialysate solution to said dialyzer means and means for discharging waste impurity-enriched dialysate solution from said dialyzer means forming a dialysate solution flow circuit including a flexible resilient tubing pumping section through which dialysate solution is pumped; dual peristaltic pump means each with a rotatable pump head assembly including a base member positioned for rotation about a fixed axis with a plurality of circumferentially spaced apart rollers mounted thereon for independent rotation about respective axes parallel to the base member fixed axis; means for anchoring the end segments of the flexible resilient tubing pumping sections in said blood flow circuit and said dialysate solution flow circuit such that the tubing in each circuit is tensionally extended around the pump head assembly of one of said peristaltic pump means and is simultaneously engaged and compressed by at least two of said circumferentially spaced apart rollers of the peristaltic pump means for said circuit with at least partial closure of the tubing at the points of compression, the rollers of each peristaltic pump means being mounted for longitudinal movement of the points of compression along the associated tubing during rotation of said pump assembly to advance fluid through said tubing; the improvement wherein said dialysate flow circuit includes a modularized dialysate solution manifold assembly and tubing segments of said dialysate solution flow circuit for flowing dialysate solution to and discharging dialysate solution from said manifold assembly, said manifold assembly comprising;

(a) a base support plate member with main flat top and bottom surfaces having spaced-apart dialysate solution inlet and outlet openings therein, with coupling means associated with said inlet and outlet openings on the main top surface of said base support plate number for detachably joining the manifold assembly with said dialysate solution tubing segments;

(b) means positioned on the main bottom surface of said base support plate member comprising a tubular passage having an inlet end communicating with said dialysate solution inlet opening for flow of dialysate solution therethrough to an outlet end of said tubular passage and means for heating said dialysate solution in said tubular passage to form warm dialysate solution;

(c) means for sensing the temperature of said warm dialysate solution positioned downstream from said heating means and for adjusting the rate of heating of said dialysate solution by said heating means in response to said temperature sensing to maintain a predetermined dialysate solution temperature level;

(d) a flow enclosure means positioned on the main bottom surface of said base support plate member containing a dialysate solution flow passage having an inlet joined to the outlet end of said tubular passage of (b) and having an outlet communicating with said dialysate solution outlet opening for flow of dialysate solution therethrough, with monitor sensing means position in said dialysate solution flow passage including: means for detecting blood leakage into said dialysate solution, means for sensing the electrolytic conductivity of said dialysate solution, and means for sensing said dialysate solution temperature, wherein said dual peristaltic pump means, anchoring means, pump drive means, and said modularized dialysate solution manifold assembly are mounted for service in a unitary enclosure, and said modularized dialysate solution manifold assembly is detachably mounted in said unitary enclosure, whereby said manifold assembly may readily be detached from said dialysate solution tubing segments and separably removed from the remainder of said hemodialysis apparatus in said unitary enclosure.

* * * * *